United States Patent [19]
Walker

[11] Patent Number: 5,148,920
[45] Date of Patent: Sep. 22, 1992

[54] PACKAGE AND PACKAGE INSERT
[75] Inventor: Michael R. Walker, Warsaw, Ind.
[73] Assignee: Zimmer, Inc., Warsaw, Ind.
[21] Appl. No.: 670,807
[22] Filed: Mar. 18, 1991
[51] Int. Cl.⁵ .................................. B65D 81/10
[52] U.S. Cl. ............................. 206/588; 206/438;
206/523; 206/592; 206/594
[58] Field of Search ............... 206/521, 523, 588, 591,
206/592, 594, 438, 524

[56] References Cited
U.S. PATENT DOCUMENTS

| | | |
|---|---|---|
| 3,013,656 | 12/1961 | Murphy . |
| 3,285,411 | 11/1966 | English, Jr. ............... 206/524 |
| 3,415,364 | 12/1968 | Schneider ................. 206/524 |
| 3,435,946 | 4/1969 | Sobek et al. ............... 206/523 |
| 3,485,347 | 12/1969 | McGill et al. .............. 206/524 |
| 3,854,650 | 12/1974 | Henave ..................... 206/521 |
| 3,987,956 | 10/1976 | Congleton ................. 206/523 X |
| 4,211,325 | 7/1980 | Wright ..................... 206/438 |
| 4,216,860 | 8/1980 | Heimann ................... 206/370 |
| 4,240,240 | 12/1980 | Cohen ...................... 206/523 X |
| 4,697,703 | 10/1987 | Will ........................ 206/438 |
| 4,700,832 | 10/1987 | Champ ..................... 206/523 X |
| 4,730,726 | 3/1988 | Holzwarth ................. 206/204 |
| 4,750,619 | 6/1988 | Cohen et al. .............. 206/438 |
| 4,763,791 | 8/1988 | Halverson et al. .......... 206/570 |
| 4,949,840 | 8/1990 | Brown ...................... 206/523 X |
| 4,953,705 | 9/1990 | Evamy ...................... 206/594 |
| 4,972,954 | 11/1990 | Dickle ..................... 206/523 |
| 5,024,328 | 6/1991 | Bontrager .................. 206/523 X |

FOREIGN PATENT DOCUMENTS

| | | | |
|---|---|---|---|
| 2591999 | 6/1987 | France ..................... 206/523 |
| 2218406 | 11/1989 | United Kingdom ........ 206/523 |

Primary Examiner—Bryon P. Gehman

[57] ABSTRACT

A package for a product includes a receptacle containing an opening and defining a space for the product and an insert defining an aperture for the product. When the product is fitted into the insert and the insert is fitted into the receptacle, a portion of the insert is between the product and the opening, thereby providing positive restraint to motion of the product relative to the insert toward the opening.

5 Claims, 2 Drawing Sheets

PACKAGE AND PACKAGE INSERT

BACKGROUND OF THE INVENTION

The present invention relates to packaging materials and, more specifically, to packages with inserts and corresponding receptacles for receiving and securing products. The package configuration of this invention is particularly suitable for use with fragile items or those items requiring protection of their surfaces, such as medical implants and instruments.

Foam envelopes or liners are often used to separate the product from its container as in U.S. Pat. No. 4,750,619. They do not, however, effectively immobilize the product. In addition, they are usually thin and therefore allow the product to be in close proximity to the container, allowing shock to be transmitted to the product and potentially rupture the container.

Container liners with formed depressions are also common. They can consist of cushions for specific portions of products, in this case functioning much like those in the electronic industry for separating an appliance from its carton. They also can be extensive and fill the container as in U.S. Pat. No. 4,763,791. Both of these are difficult to make and expensive relative to the present invention. While they can be changed to provide package flexibility, it is not advantageous as they are among the most expensive components of the package.

Another package configuration contains a rigid formed tray such as in U.S. Pat. Nos. 4,730,726, 4,216,860 and 3,013,656. These trays have cavities formed to generally correspond to the product shape. However, they depend on product-to-container contact resulting in abrasion of the product, abrasion of the package, and possible rupture of the package. Finally, they fail to provide inexpensive package adaptability.

U.S. Pat. No. 4,697,703 teaches a joint prosthesis package containing two inserts that snap into the top and bottom of a container. These two inserts have projections that cooperate to trap a medical item therebetween. This configuration requires multiple parts with complicated geometries and tight manufacturing tolerances. The tooling and processing required to produce these parts as well as their number makes this package expensive relative to the present invention.

Recited in U.S. Pat. No. 4,211,325 is a heart valve holder with a multiplicity of parts comprising a case, a valve support ring and a cap. The cap is necessary to provide positive containment of the valve. Further, the heart valve holder structure is such that the valve must be grasped to effect its removal, exposing it to damage as it is pulled from the case. Finally, the holder components are difficult to make and expensive relative to the present invention.

SUMMARY OF THE INVENTION

The invention of this disclosure addresses the deficiencies of the above-mentioned packages by providing a package configuration including an inexpensive insert containing an aperture for receiving the product. This insert, when fitted into an appropriate receptacle, securely holds the product and protects it from abrasion and shock. It also accommodates a variety of sizes of a particular product. Further, by simply changing the insert, the same receptacle can be used for differently shaped products. In addition, embodiments of this invention provide ready access to the product, reduced package size and reduced raw material consumption. Finally, the insert provides these advantages while at the same time being particularly suited to inexpensive manufacturing processes.

BRIEF DESCRIPTION OF THE DRAWINGS

The before mentioned features and advantages of the present invention are apparent from the following detailed description and the drawings wherein.

DETAILED DESCRIPTION OF THE INVENTION

Figure 1:
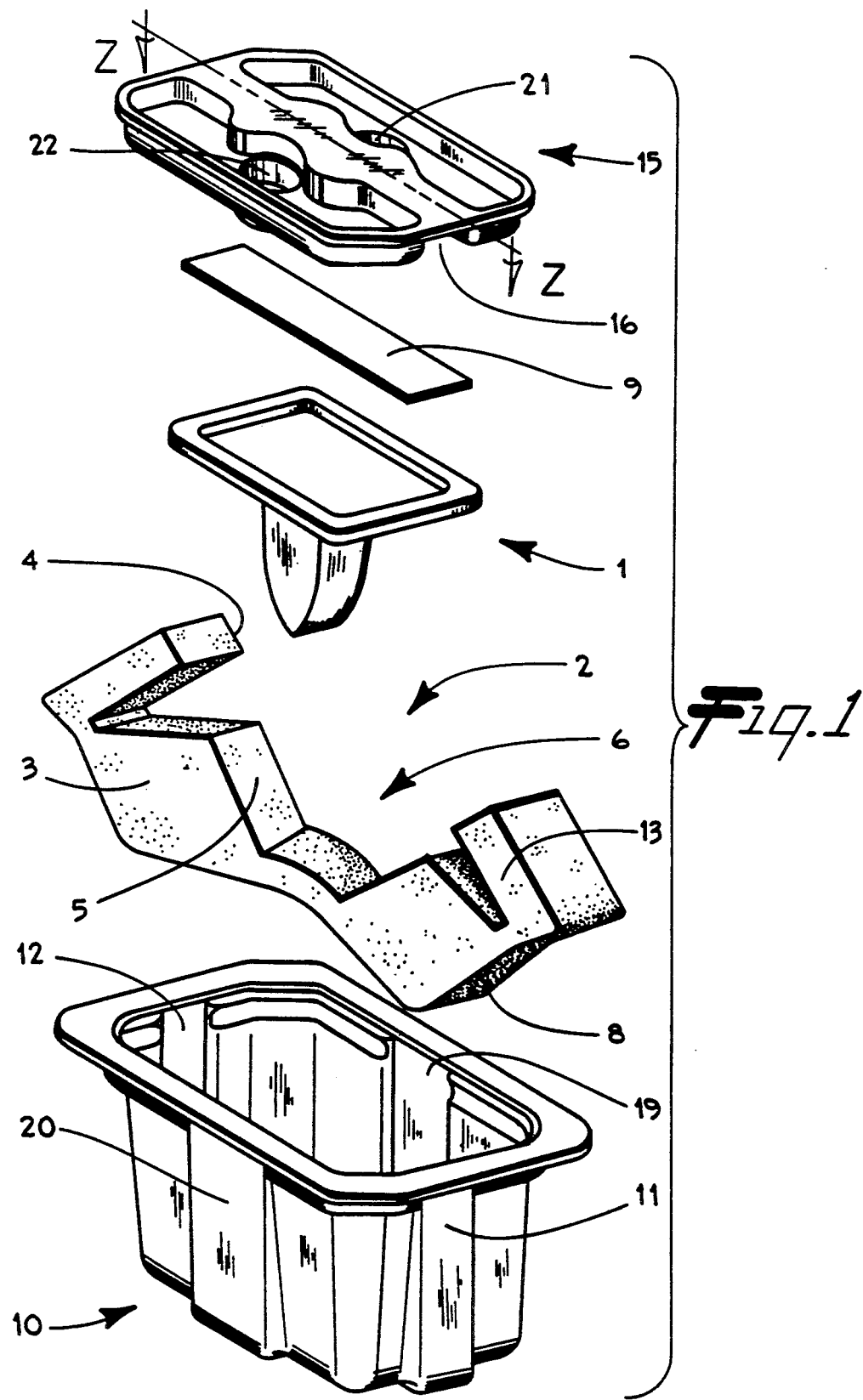
FIG. 1 is an exploded perspective view of the preferred embodiment of the invention.
Figure 2:
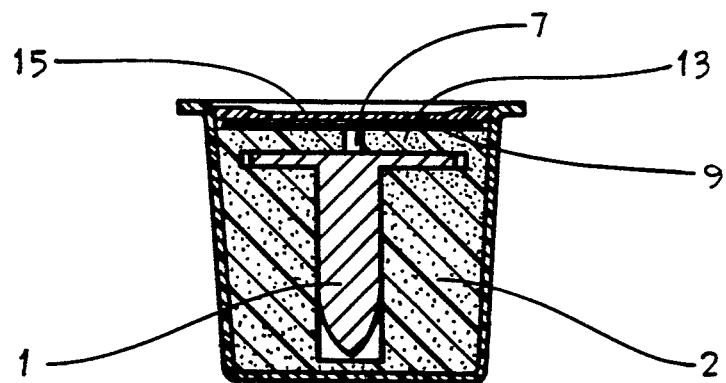
FIG. 2 is a section view of the assembled embodiment of FIG. 1.

Referring to FIG. 1 medical product 1 is shown with an insert 2 in accordance with the present invention. The insert 2 is shown flexed into an open position in which the product 1 can be easily inserted and removed. The insert 2 comprises a front surface 3, an opposing back surface 4, an inner edge 5, and an outer edge 8. The inner edge 5 extends through the insert 2 from the front surface 3 to the back surface 4 to define an aperture 6 in which medical product 1 is disposed. The aperture's pre-formed shape substantially corresponds to the cross sectional shape of the product thereby dictating the orientation of the product within the insert and preventing motion or malplacement of the product within the insert. The insert 2 may be formed of any suitable material. However, for the preferred embodiment shown in FIG. 1, a flexible, resilient material such as a cross-linked polyethylene foam is desirable. This material is sufficiently deformable to conform to the shape of the product 1 and thereby form a positive grip on it. In conforming to the product 1 shape it may be possible and is acceptable for the insert 2 to close around the product 1 and obscure it from view. Some combinations of product 1 and insert 2 may not produce a positive grip, in which case it is desirable for the combination to exhibit a sufficiently high coefficient of friction to hold the product within the liner 2. It is also desirable to make the insert 2 by an inexpensive process such as die cutting, hot wire cutting, or other suitable process. The preferred insert 2 is provided with a break 7 communicating between the inner edge 5 and the outer edge 8 (see FIG. 2). It is this break 7 that allows the insert 2 to be flexed into the open position shown. When the product 1 is disposed in the insert 2 a releasable closure 9, separate from the receiving means, such as a piece of adhesive tape, may be utilized to hold the insert 2 in a closed position in which the product is securely held. In the closed position the product is substantially encircled in a cross-sectional plane, whereby an insert acting on the cross-sectional plane can securely support the product. This closure prevents the insert 2 from prematurely releasing its grip on the product 1. The product 1 may further be enclosed by placing the insert 2 into a receptacle 10, preferably a container with an opening and grooves 11 and 12 to hold the insert relative to the container. Referring to FIG. 2, where the product 1 is thus disposed, a portion 13 of the insert 2 is between the product 1 and the opening of the receptacle 10, thereby providing positive restraint to motion of the product 1 relative to the insert 2 toward the opening. A lid 15 may be provided to retain the insert 2 in the receptacle 10. The lid 15 may preferably include a channel 16 cooperating with grooves 11 and 12 to hold the insert 2. The portion 13 may be formed as a distinct part of the insert 2 during its manufacture as shown, or the portion 13 may result from the insert deforming to conform to the product 1 or to conform to other package components such as the receptacle 10 or lid 15 such that the portion 13 of the insert 2 comes to be between the product 1 and the opening of the receptacle 10 when the package is assembled.

While the foregoing has described a preferred embodiment of the package configuration of the present invention, variations in design and construction are possible. For example, while the insert 2 is depicted as a relatively thick foam structure, it may be thicker or thinner as required or desired. It may also be constructed of a more or less rigid material as appropriate for the situation.

The receptacle 10 is depicted as a one-piece box whereas it may comprise a folding cardboard carton, an envelope or any other suitable means. It is also shown with two sets of grooves for positioning the insert 2; the first pair is indicated at 11 and 12 and the second pair is indicated at 19 and 20. However, it may contain no grooves or multiple sets of grooves. When more than one set of grooves is combined with a receptacle 10 of non-square plan section, the same receptacle 10 will accept different sizes of inserts 2, a smaller insert fitting in grooves 19 and 20 and a larger insert fitting in grooves 11 and 12. Lastly, the receptacle 10 may be sufficiently large that the product 1, which may extend outwardly from the insert 2, does not contact the receptacle; thereby effectively isolating the product 1 from all but the insert 2.

Figure 3A:
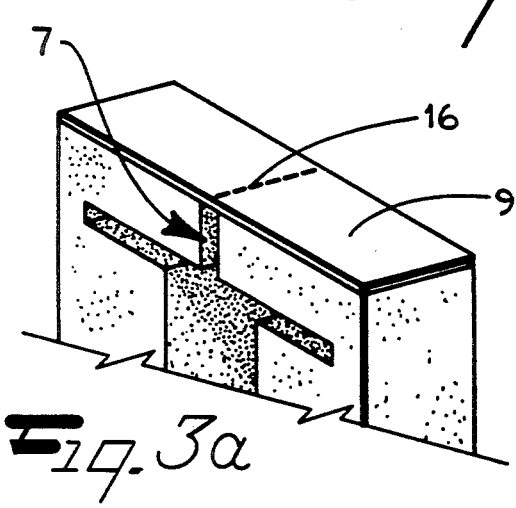
FIGS. 3a through 3c are perspective views of alternate embodiments of a closure.
Figure 3B:
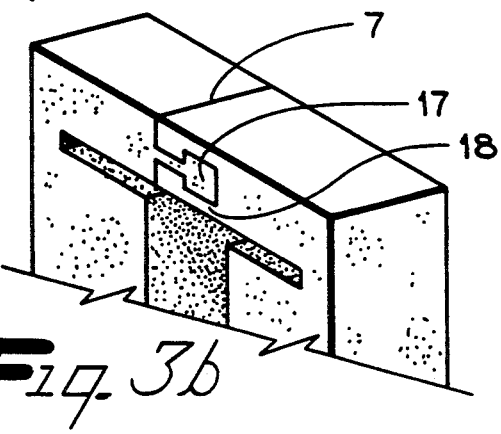
Figure 3C:
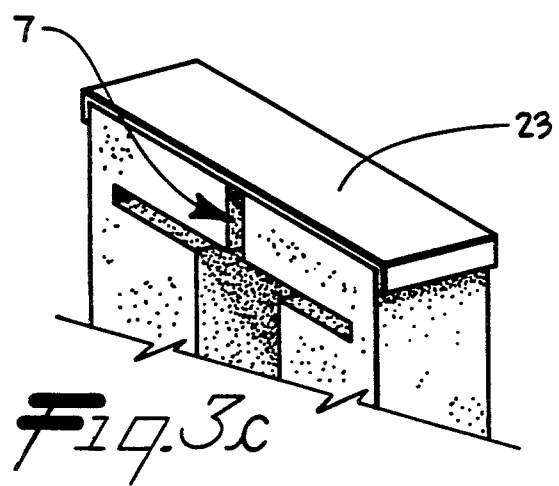

The closure 9 may also be modified as shown in FIGS. 3a through 3c. FIG. 3a shows adhesive tape with a perforation 16 to aid in breaking it to remove the product 1. FIG. 3b shows a closure with a tab 17 and slot 18 formed in the insert material. FIG. 3c shows a clip 23 used as a closure and held in place by spring force against the outer edge. The closure, regardless of its configuration, may further be imprinted with instructions for use or other information.

Turning to the lid 15, it may, like the receptacle 10, contain no channels, one channel 16 or multiple channels. It may also be formed to snap into place on the receptacle and may include gripping means such as the depressions shown at 21 and 22. The lid 15 further may form a connection with the insert 2 so that the lid 15 and insert 2 may be removed from the receptacle 10 as a unit (not shown). This connection may take the form of an interlocking extension from the insert 2 through a hole in the lid 15, an extension from the lid 15 into the insert 2, an adhesive bond between the lid 15 and insert 2 or any other suitable connection.

While the drawings illustrate the package configuration of the present invention holding a tibial component for use in total knee arthroplasty, other embodiments within this invention's scope could as readily hold other medical products or, for that matter, any article medical or otherwise that requires packaging. It will be understood by those skilled in the art that the aforementioned modifications and numerous others may be made to the preferred embodiment without departing from the spirit and scope of the invention defined by the appended claims.

I claim:

1. A package for a product including;
    a bottom with upwardly extending opposed walls forming a cavity with an opening at its top, wherein two opposed walls each contain a groove;
    an insert comprising a front surface, a back surface, an inner edge, and an outer edge, wherein a portion of the outer edge fits within the grooves and the inner edge extends from the front surface to the back surface to define an aperture within which a said product may be disposed, the aperture having a pre-formed shape corresponding substantially to a said product's cross-sectional shape such that when a said product is fitted into the insert and the insert is fitted into the grooves a portion of the insert is between a said product and the opening, thereby providing positive restraint to motion of a said product relative to the insert toward the opening.

2. The package of claim 1 wherein the cavity is larger than a said product such that when the insert is fitted into the grooves, a said product is maintained in spaced relationship from the walls.

3. The package of claim 1 wherein a pair of the walls face each other to define a first dimension and another pair of walls face each other to define a second dimension which is different from the first dimension.

4. The package of claim 1 further comprising a lid for the opening.

5. A package for a product including;
    a bottom with upwardly extending walls forming a cavity with an opening at its top, wherein the walls form a groove;
    an insert comprising a front surface, a back surface, an inner edge, and an outer edge, wherein a portion of the outer edge fits within the groove and the inner edge extends from the front surface to the back surface to define an aperture within which a said product may be disposed, the aperture having a pre-formed shape corresponding substantially to a said product's cross-sectional shape such that when a said product is fitted into the insert and the insert is fitted into the groove, a portion of the insert is between a said product and the opening, thereby providing positive restraint to motion of a said product relative to the insert toward the opening;
    a lid for the opening, the lid having a channel aligning with the groove.

* * * * *